United States Patent
Hammer et al.

(10) Patent No.: US 6,923,171 B2
(45) Date of Patent: Aug. 2, 2005

(54) DEVICE AND METHOD FOR DETERMINING THE ORIENTATION OF A CRYSTALLOGRAPHIC PLANE IN RELATION TO A CRYSTAL SURFACE AND DEVICE FOR CUTTING A SINGLE CRYSTAL IN A CUTTING MACHINE

(75) Inventors: Ralf Hammer, Freiberg (DE); Ralf Gruszynsky, Brand-Erbisdorf (DE); André Kleinwechter, Freiberg (DE); Tilo Flade, Freiberg (DE)

(73) Assignee: Freiberger Compound Materials GmbH, Freiberg (DE)

( * ) Notice: Subject to any disclaimer, the term of this patent is extended or adjusted under 35 U.S.C. 154(b) by 0 days.

(21) Appl. No.: 10/480,560

(22) PCT Filed: Jun. 11, 2002

(86) PCT No.: PCT/EP02/06407

§ 371 (c)(1),
(2), (4) Date: Dec. 11, 2003

(87) PCT Pub. No.: WO02/100619

PCT Pub. Date: Dec. 19, 2002

(65) Prior Publication Data

US 2004/0168682 A1 Sep. 2, 2004

(30) Foreign Application Priority Data

Jun. 13, 2001 (DE) .......................................... 101 28 630

(51) Int. Cl.$^7$ .................................................. B28D 1/06
(52) U.S. Cl. ..................................... 125/16.02; 125/21
(58) Field of Search ........................... 125/16.01, 16.02, 125/21, 35; 83/651.1, 418

(56) References Cited

U.S. PATENT DOCUMENTS

| | | | |
|---|---|---|---|
| 3,202,041 A | | 8/1965 | Bernhardt |
| 4,771,759 A | | 9/1988 | Zoebeli |
| 5,529,051 A | | 6/1996 | Miller |
| 5,735,258 A | * | 4/1998 | Okuno et al. ............ 125/16.02 |
| 5,768,335 A | | 6/1998 | Shahid |
| 5,839,425 A | | 11/1998 | Toyama et al. |
| 5,857,454 A | | 1/1999 | Shibaoka |
| 5,878,737 A | | 3/1999 | Hodsden |
| 5,893,308 A | | 4/1999 | Katamachi et al. |
| 5,904,136 A | | 5/1999 | Shibaoka et al. |
| 6,055,293 A | | 4/2000 | Secrest |
| 6,056,031 A | | 5/2000 | Shimizu et al. |
| 6,145,422 A | | 11/2000 | Katamachi et al. |

FOREIGN PATENT DOCUMENTS

| | | |
|---|---|---|
| DE | 1114649 | 4/1962 |
| DE | 3305695 | 8/1984 |
| DE | 0243215 | 10/1987 |
| DE | 100 52 154 A1 | 5/2002 |
| EP | 0 242 489 | 10/1987 |
| EP | 1 041 179 A1 | 10/2000 |
| JP | 55062742 A | 5/1980 |
| JP | 60197361 | 10/1985 |
| JP | 03010760 | 1/1991 |
| JP | 10193338 | 7/1998 |
| JP | 11002614 A | 1/1999 |
| JP | 11064252 | 3/1999 |

* cited by examiner

Primary Examiner—Dung Van Nguyen
(74) Attorney, Agent, or Firm—George W. Neuner; Edwards & Angell LLP

(57) ABSTRACT

An apparatus and a method for determining the orientation of a crystallographic plane (100) relative to a crystal surface (2) are provided, in which the orientation is free from errors of adhesion of the crystal or contamination of the holders for the crystal. For this purpose, the angle which the crystal surface to be measured forms with a reference axis and the angle which the crystallographic plane forms with the reference axis are measured and subtracted. In a wire sawing apparatus with an X-Y positioning unit, next the desired correction is made with the aid of measurement of the orientation and at the same time the crystal is displaced in horizontal and vertical positions. As a result, there remains a further degree of freedom of rotation of the crystal in the cutting plane for achieving a cut which is free from forces perpendicular to the feed direction and wire direction, so that no tool deflection takes place or the cutting forces are minimal. Further, the precision of orientation is increased.

23 Claims, 6 Drawing Sheets

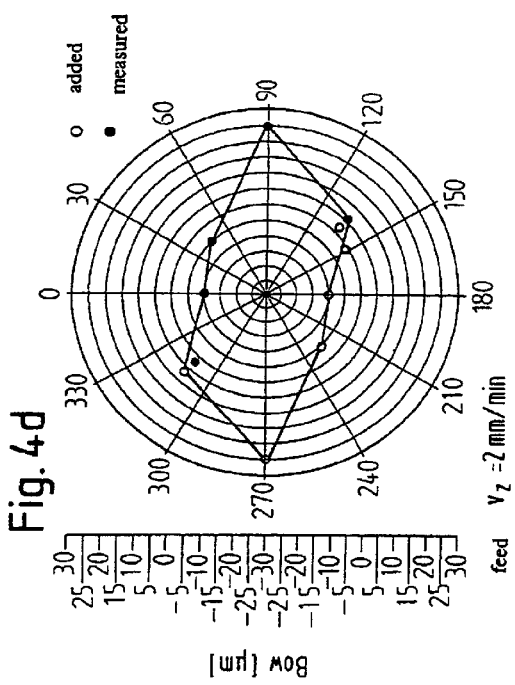
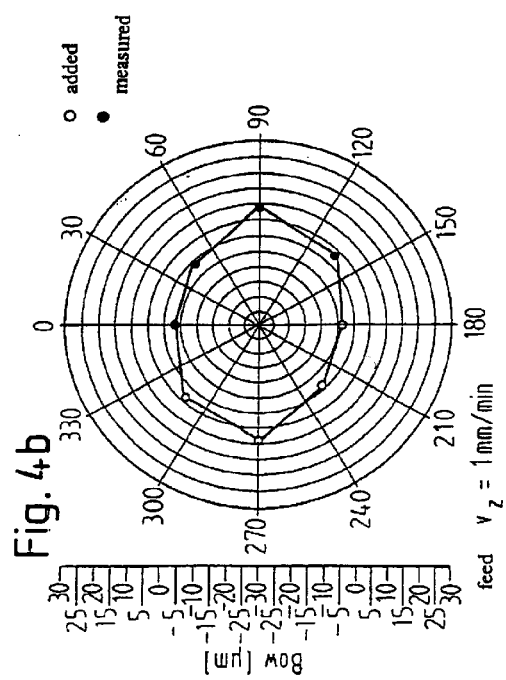
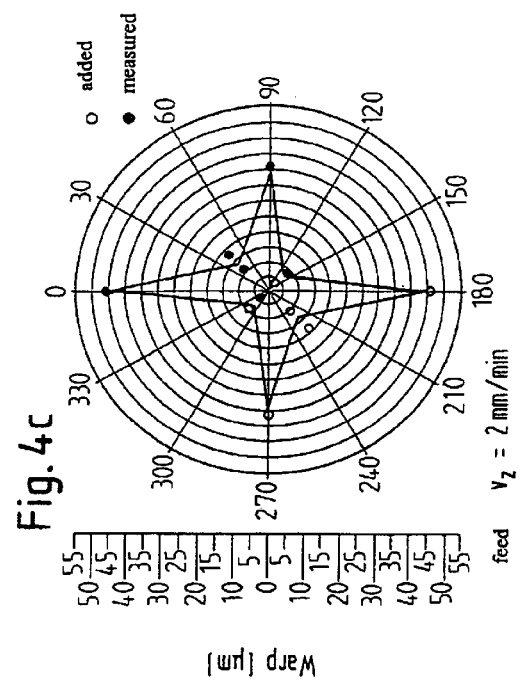
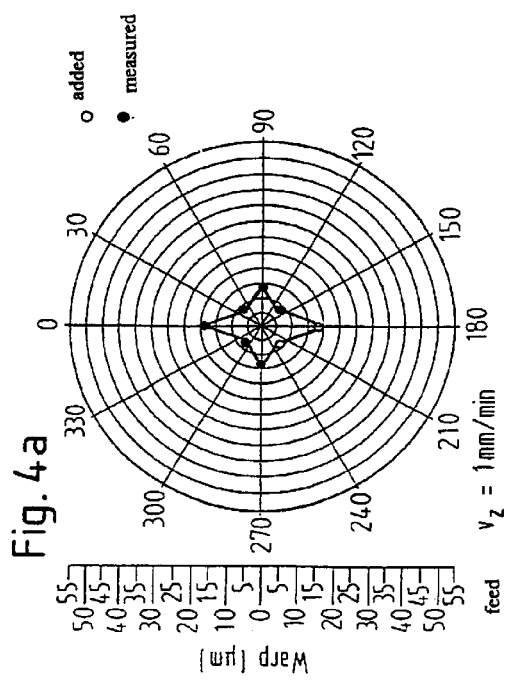

DEVICE AND METHOD FOR DETERMINING THE ORIENTATION OF A CRYSTALLOGRAPHIC PLANE IN RELATION TO A CRYSTAL SURFACE AND DEVICE FOR CUTTING A SINGLE CRYSTAL IN A CUTTING MACHINE

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not Applicable

BACKGROUND OF THE INVENTION (1) Field of the Invention

The invention concerns an apparatus and a method for determining the orientation of a crystallographic plane relative to a crystal surface as well as an apparatus and a method for cutting a single crystal in a cutting machine.

(2) Description of Related Art

For certain applications, semiconductor wafers with so-called misorientation are needed. As can be seen from FIG. 1, in a semiconductor wafer 1 with misorientation a certain crystallographic plane, e.g. the (100) plane, is not parallel to the wafer surface 2. The angle of misorientation $\phi$ is in this case the angle which the vector [100] which is perpendicular to the (100) plane forms with the normal vector $N_0$ which is perpendicular to the wafer surface 2. If such misorientation is needed, then a single crystal from which the wafers are cut is tilted by the predefined angle $\phi$ about an axis T located in the cutting plane, i.e. the wafer surface 2.

With the known method of inner hole sawing, to produce such misorientation the orientation of the crystal which is stuck on a work piece holder is measured with an X-ray goniometer by measuring the position of the Bragg reflection relative to the work piece holder. By means of this holder, holding is effected on the inner hole cutting saw which has a horizontally and vertically displaceable support on which the measured orientation of the crystal can be corrected or adjusted to the desired value. The first wafer cut off is again measured on an X-ray goniometer, and the support is recorrected if necessary. Imprecisions in orientation which arise when the work piece holder is inserted in the inner hole sawing apparatus can thus be eliminated only by repeated measurement and recorrection.

With the known method of wire sawing, such correction by remeasuring and reorientation is not possible, because all the wafers are cut from a single crystal simultaneously. As can be seen from FIG. 2a, in wire sawing a single crystal 3 is held in a holder, not shown in FIG. 2a, which is movable by a drive of a feed unit towards the wire area 4 of a wire saw at a feed rate v and back to the starting position. The wire saw consists of a plurality of parallel wires 4a, 4b, 4c which are lightened by means of rollers, not shown in FIG. 2, and movable in planes perpendicular to the longitudinal centre axis M of the single crystal 3 in the directions shown by the arrows A and B in FIG. 2a. The wire sawing apparatus further includes devices 5 and 6 for applying a paste containing silicon carbide particles to the wires 4a, 4b, 4c on each side of the single crystal 3. In wire sawing with electrically bound cutting particles, a device for applying a cooling lubricant is further provided.

Wire saws are known with an orienting unit which for adjustment of the desired misorientation, as can be seen in FIG. 2b, allows exclusively displacement in a plane parallel to the plane of the wire area 4. For this purpose the crystal is measured outside the wire saw on an X-ray goniometer and stuck to a work piece substrate in such a way that the misorientation to be set lies in the horizontal plane, that is, the angle $\phi$ shown in FIG. 1 in a plane parallel to the wire area 4. The measurements of the X-ray goniometer in this case relate to a stop face of the work piece substrate, which is then applied to a reference face on the wire saw. Then the desired orientation is set horizontally. With this method, however, errors due to contamination of the stop and reference faces as well as adhesion errors which arise when the single crystal is stuck to the work piece substrate are not detected, as orientation measurement takes place outside the machine. Further, the single crystal must always be turned in such a way that the misorientation to be set lies in the horizontal plane parallel to the wire area 4. As a result, the direction of processing is governed by the required misorientation and can therefore vary from one single crystal to the next.

It is known from U.S. Pat. No. 5,904,136 that the required tilt angle for setting the misorientation can be performed in a tilting device outside a wire sawing apparatus, wherein the crystal orientation is determined with an X-ray device and then the crystal is tilted in the tilting device in horizontal and vertical directions relative to the wire area. Possible errors upon insertion of the tilting device together with the crystal in the wire sawing apparatus therefore likewise cannot be eliminated, however.

It is the object of the invention to provide an apparatus and a method for determining the orientation of a crystallographic plane relative to a crystal surface as well as an apparatus and a method for cutting a single crystal in a cutting machine, with which it is possible to carry out precise cutting and at the same time increase the yield of wafers during cutting of the single crystal.

SUMMARY OF THE INVENTION

The present invention provides an apparatus for cutting single crystals comprising: a cutting device (4) for cutting off wafers from an essentially cylindrical single crystal (3) having a longitudinal centre axis (M); an orienting device (24) provided in the apparatus for orienting the single crystal relative to the cutting device; a feed device (23) for moving the crystal (3) in a feed direction (V) essentially perpendicular to its longitudinal centre axis relative to the cutting device; characterised in that the orienting device (24) is designed in such a way that the single crystal (3) is rotatable about an axis defined by the feed direction and an axis which is perpendicular to the plane which is defined by the longitudinal centre axis (M) and the feed direction (V).

The invention also provides an apparatus for determining the orientation of a crystallographic plane relative to a crystal surface, comprising: a holder (11) for the single crystal (3) with which the single crystal (3) is held in such a way that its surface (2) to be measured is exposed; an angle measuring device (14, 17) for measuring the angle which the surface (2) to be measured has relative to a reference axis of the holder; and an X-ray measuring device (15, 16) for determining the angle of the crystallographic plane relative to the reference axis.

In addition, the invention provides a method for cutting a single crystal in a cutting machine in which wafers are cut off from the single crystal by movement of the single crystal in a feed direction (V) relative to a cutting device, with the steps of: determining the angle between the crystallographic plane and an external surface (2) of the single crystal; measuring the orientation of the external surface (2) of the single crystal in the cutting machine; positioning the single crystal on the basis of the orientation of the external surface in such a way that the given crystallographic plane forms with the feed direction a predetermined angle; and carrying out cutting.

Further, the invention provides a method for determining the orientation of a crystallographic plane relative to a crystal surface, comprising the steps of: measuring the angle which the crystal surface (2) forms with a reference axis by an autocollimation method; measuring the angle of the crystallographic plane relative to the reference axis by X-ray goniometry; and subtracting the measured angles.

Preferred embodiments of the apparatus in accord with the present invention include one or more of the following features:

the cutting device is designed as a wire saw having a plurality of parallel wires (4) which form a wire plane, for cutting, and in that the orienting device (24) is designed as an X-Y positioning unit with which the single crystal is displaceable in a plane parallel to the wire plane and a plane perpendicular to the wire plane;

an angle measuring device is provided for measuring the orientation of an end face (2) of the single crystal (3) relative to the wire plane;

the angle measuring device comprises a mirror (27) which can be fixed to the end face (2) of the single crystal (3), and an autocollimation telescope (25) whose optical axis (O) is perpendicular to the cutting plane;

the mirror (27) can be attached to the end face (2) of the single crystal by means of a vacuum device;

a reference device (32, 25) is provided for the X-Y positioning unit;

a wedge plate (28) having a given wedge angle is provided for adjusting a predetermined angle offset of the X-Y orientation of the single crystal;

the wedge plate (28) is rotatable in the cutting plane about the longitudinal centre axis of the single crystal in such a way that a given azimuthal orientation of the wedge angle is adjustable;

a holder (12) is provided for the single crystal, with which the single crystal is positioned in the cutting apparatus in such a way that a predetermined external feature of the single crystal is oriented in a predetermined position rotated about the longitudinal centre axis (M);

a rotating device is provided for rotating the single crystal about its longitudinal centre axis and in that preferably there is a device for measuring the deflection of the cutting device during cutting, which is coupled to the rotating device;

a device for determining the orientation of a crystallographic plane relative to a crystal surface, wherein the device comprises: a holder (11) for the single crystal (3) with which the single crystal (3) is held in such a way that its surface (2) to be measured is exposed, an angle measuring device (14, 17) for measuring the angle which the surface (2) to be measured has relative to a reference axis of the holder; and an X-ray measuring device (15, 16) for determining the angle of the crystallographic plane relative to the reference axis;

the single crystal (3) is essentially cylindrical and the surface (2) to be measured is an end face of the cylinder, and the holder (11) comprises a plane surface (11a) to which the single crystal (3) can be fixed with its end face opposite the surface to be measured, and in that the reference axis is the normal to the plane surface (11a);

the angle measuring device (14, 17) includes a mirror (17) arranged on the surface (2) to be measured and an autocollimation telescope (14) whose optical axis (O) coincides with the reference axis;

the X-ray measuring device is designed as an X-ray goniometer which includes an X-ray tube (15) and a detector (16) which are movable together within an angular range about the reference axis for measuring Bragg reflections for the crystallographic plane;

the holder (11) is movable in the direction of the reference axis;

the holder (11) comprises a vacuum suction device for fixing the single crystal (3) by means of partial pressure or vacuum; and the single crystal in the holder comprises a stop (13) with which the single crystal (3) can be fixed in a predetermined angular orientation in a plane perpendicular to the reference axis, wherein preferably a stop (13) is provided.

Preferred embodiments of the method in accord with the present invention include one or more of the following features:

measuring the angle which the crystal surface (2) forms with a reference axis by an autocollimation method, measuring the angle of the crystallographic plane relative to the reference axis by X-ray goniometry, and subtracting the measured angles; and the angular position of a given crystallographic direction (K) of the single crystal in the cutting plane is adjusted in such a way that during cutting of the single crystal the forces acting on the cutting device are minimised.

The method and the apparatus have the advantage that the quality of the wafers is increased and that higher feed rates during cutting are made possible. Due to the improved quality of the wafers produced, further processing steps which are otherwise commonplace can be largely eliminated. Further, the precision of orientation can be increased.

There follows a description of an embodiment with reference to the figures.

BRIEF DESCRIPTION OF THE DRAWINGS

The figures show:

FIG. 4a a two-dimensional graphic representation of warp to 4d and bow of wire-sawn wafers as a function of the direction of processing with two different feed values;

DETAILED DESCRIPTION OF THE INVENTION

For a better understanding, first the forces acting on the wafer during wire sawing are described below with the aid of FIGS. 1 to 4. As can be seen from FIG. 3, during wire sawing the wires 4a, 4b, 4c penetrate into the single crystal 3 for cutting off wafers 1a, 1b, 1c, etc. During the cutting operation, after reaching a critical depth of penetration into the single crystal 3 the diamond particles of the wires produce microcracks which lead to removal of material due to mutual crosslinking. This critical depth of penetration depends on the orientation of a given crystallographic direction K located in the wafer surface 2, for example the [010] direction, relative to the feed direction V, which is explained below.

Figure 1:
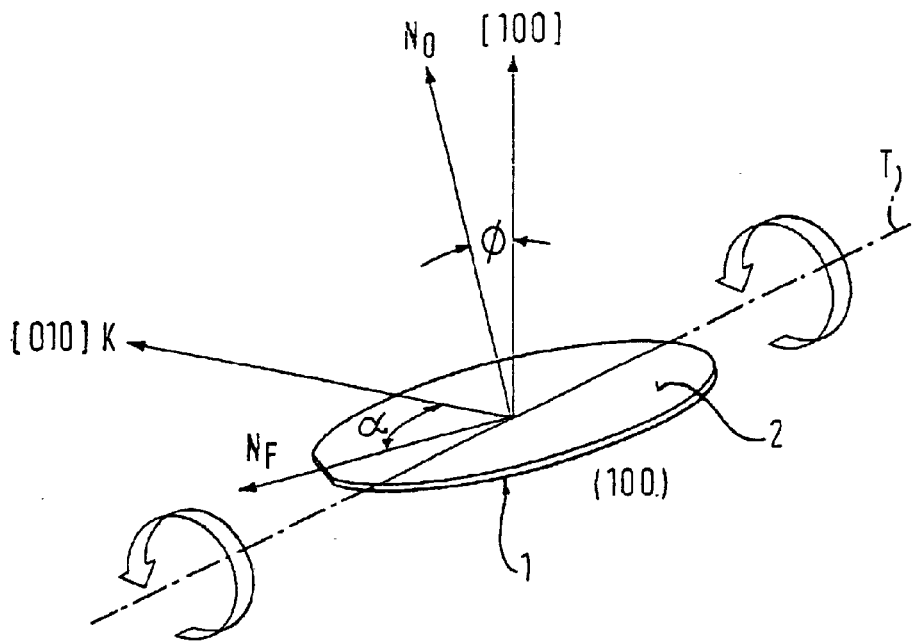
FIG. 1 a schematic view of a wafer.
Figure 2A:
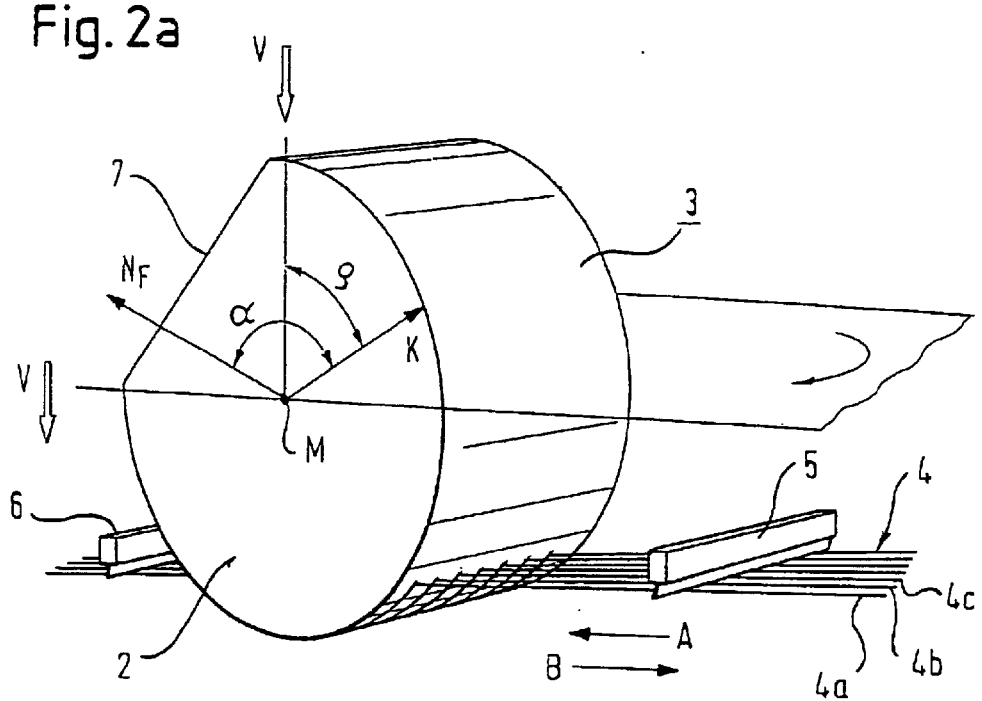
FIG. 2a a schematic view of a wire sawing apparatus with a single crystal to be cut.
Figure 2B:
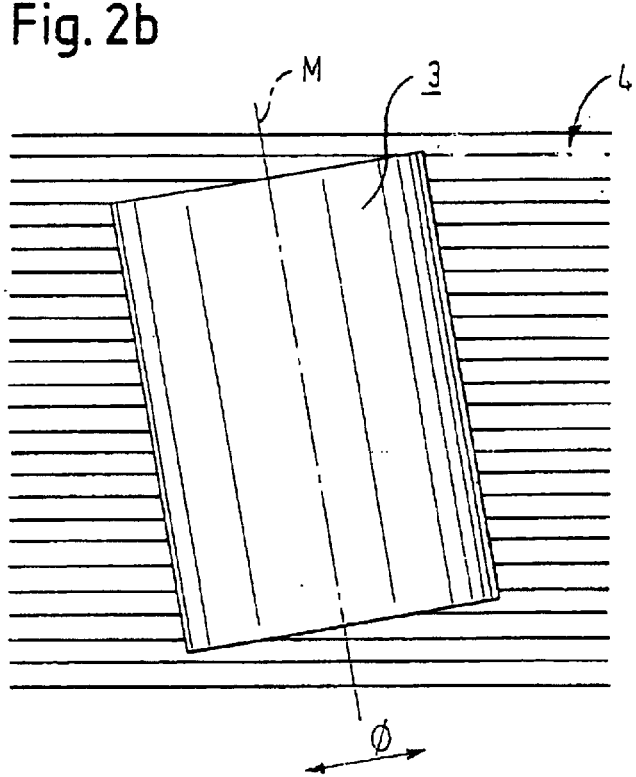
FIG. 2b a schematic view of adjustment of the misorientation in a wire sawing apparatus according to the state of the art.

As can be seen from FIGS. 1 and 2a, the single crystal 3 exhibits an orientation feature in the form of a plane outer-surface section 7, the so-called flat, which has been applied in a given manner after growing the single crystal 1 in such a way that an angle α which the given crystallographic direction K forms with the normal $N_F$ on the plane outer-surface section in the wafer surface 2 is known. As the angle α is known, an angle ρ between the given crystallographic direction K and the feed direction V of the single crystal in a plane perpendicular to the longitudinal centre axis M of the single crystal and hence in the cutting plane is therefore also known. It should be noted that, instead of the flat, an incision called a notch can be provided on the outside of the single crystal. The crucial factor is only an external feature whose arrangement relative to the given crystallographic direction K is known.

Figure 3:
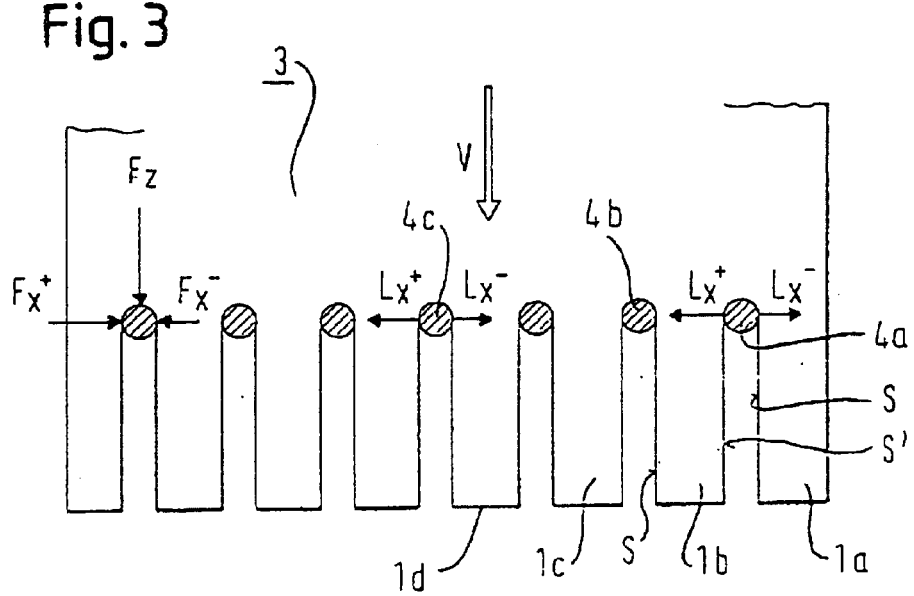
FIG. 3 a schematic view of the forces arising during wire sawing.

As can be seen from FIG. 3, during penetration of the wires 4a, 4b, 4c, etc. into the single crystal the forces $F_x^-$ or $F_x^+$ acting on each wire differ on account of different critical loads $L_x^+$ or $L_x^+$ on the front and rear sides S or S' of a wafer 1a, 1b, 1c, etc., so that the disequilibrium of forces arising leads to drift of a wire until the repelling force of the taut wire has restored the equilibrium of forces. The critical loads are physically equivalent to the critical depths of penetration. FIGS. 4a to 4d in each case show the warp or bow for a wafer as a function of the angular adjustment of the given crystallographic direction K relative to the feed direction V. It follows that a low warp or a low quantity of the bow value, which are desired, are obtained either by reducing the feed rate v or, for a high feed rate, by adjusting the angle of the crystallographic direction K relative to the feed direction. With a feed rate of 2 mm/min, for example minimum bow values around 60°, 150°, 240° and 330° are achieved. With these values, the resultant force which arises from the sum of the constraining forces $F_x^-$ or $F_x^+$ is minimal. The preferred angles at which the constraining forces described above are compensated and the wires penetrate into the single crystal without transverse deflection depend on the material of the single crystal, or in the case of semiconductors on the doping as well, and on other factors. They are to be determined empirically for each single crystal material.

The device according to the invention for orienting a single crystal in the cutting machine, in particular in the wire sawing apparatus, allows the utilisation of this effect and at the same time precise adjustment of a desired misorientation φ.

Figure 5A:
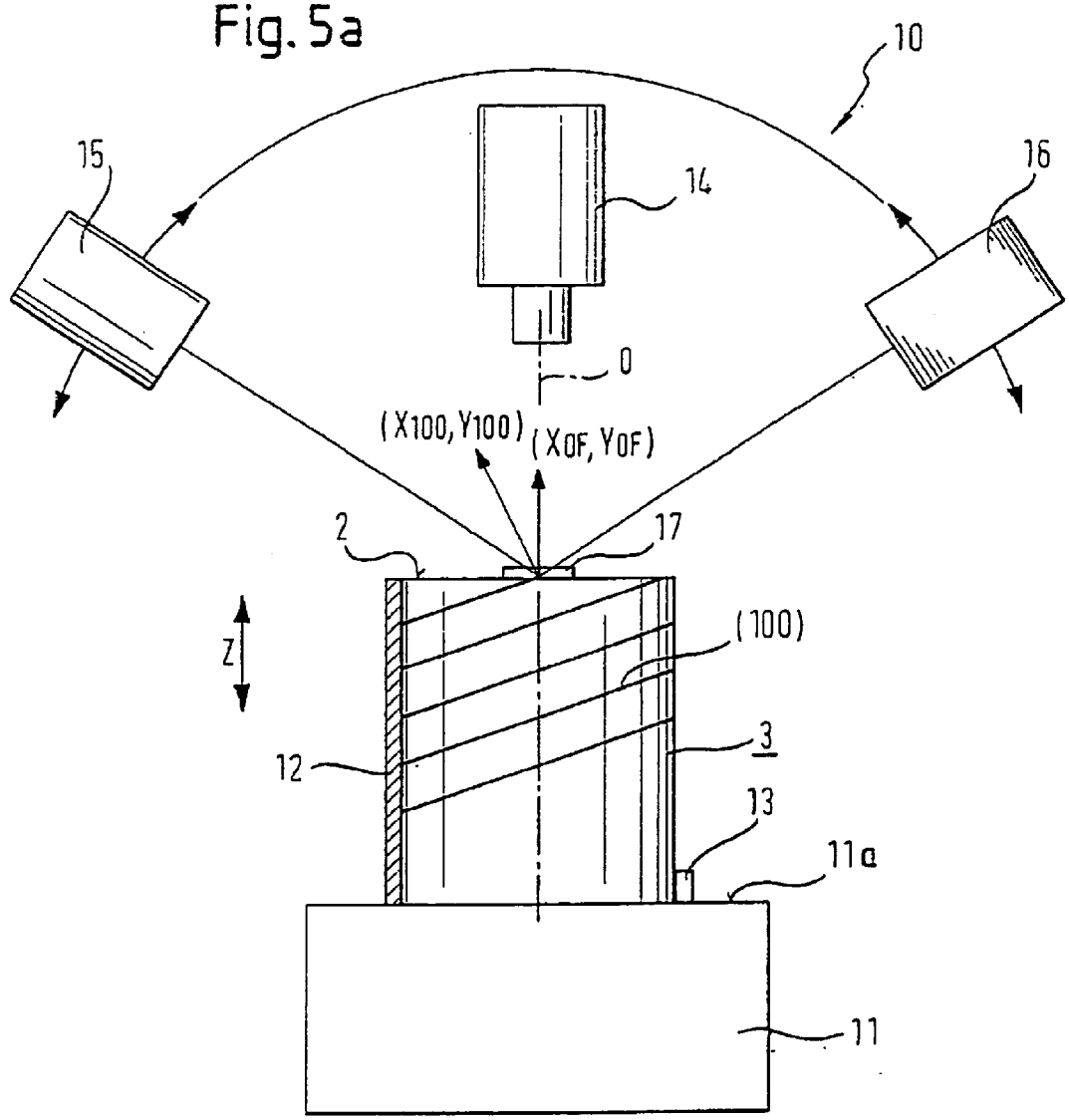
FIG. 5a a schematic view of the apparatus according to the invention for determining the orientation of a crystallographic plane relative to a crystal surface.
Figure 5B:
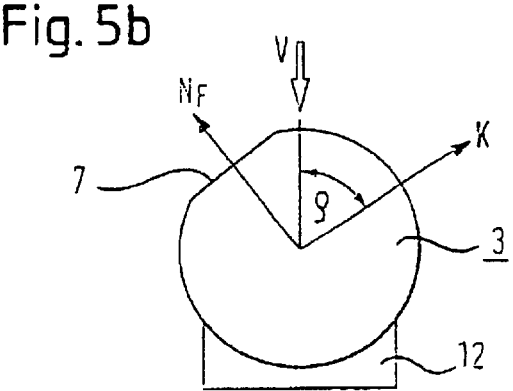
FIG. 5b a view of a single crystal inserted in a saw holder in the direction of one of the end faces.

As can be seen from FIG. 5a, the device for orienting a single crystal in a cutting machine comprises an apparatus 10 located outside the actual cutting machine for determining the angle between a crystallographic plane, for example the (100) plane, and the crystal end face 2. The apparatus 10 comprises a holder 11 for the single crystal 3 with a plane surface 11a which is preferably designed as a vacuum chuck and in which the essentially cylindrical single crystal is held at its end face by the action of partial pressure. The azimuthal orientation of the single crystal, i.e. the angular position in the subsequent cutting plane, is defined by the orientation of the flat 7 or other external feature in the apparatus 10. The single crystal 3 is in this case either stuck fast to a sawing substrate 12 with which it can later be inserted in the wire sawing apparatus, or adhesion takes place after measurement. The angular position of the flat 7 provided on the single crystal 3 relative to the holder 11 is adjusted by means of a stop 13 in such a way that the angle ρ exhibited by the given crystallographic direction K relative to the feed direction in the cutting machine, as can be seen in FIG. 5b, has an empirically predetermined value as described above, for the minimum wire deflection and hence maximum possible feed rate. The holder 11 is movable in a vertical direction. Further, the holder 11 is rotatable by means of a rotation mechanism, not shown, about its central axis which runs parallel to the longitudinal centre axis of the single crystal. Opposite or above the free surface 2 of the single crystal 3, which forms the subsequent surface of the first wafer to be cut off, is provided an autocollimation telescope 14 which is positioned so that its optical axis O coincides with the normal to the surface 11a of the holder 11. There is further provided an X-ray goniometer consisting of an X-ray tube 15 and an associated detector 16 which is movable within a predefined angular range, for example of about 20°, about a point of origin on the surface 2 of the single crystal. Further, a plane-parallel optical mirror 17 is provided. The mirror 17 can be fixed by means of a vacuum mechanism, not shown, to the end face 2 of the single crystal. The mirror 17 can further be fixed to the end face 2 of the single crystal 3 so as to lie on the optical axis of the autocollimation telescope. The range of measurement of the autocollimation telescope is approximately ±1°. In the event that the angle which the end face 2 of the crystal has relative to the plane surface 11a exceeds this range of measurement, there is provided an optical wedge plate, not shown, having a given wedge angle, which causes a given beam deflection of e.g. 2° in order to bring the surface to be measured within the range of measurement again.

Control of the apparatus 10 is designed in such a way that first an angular measurement of the mirror orientation is carried out automatically with the autocollimation telescope and then a measurement of the desired crystallographic plane, for example the (100) grate plane, with the X-ray goniometer. Control is further designed in such a way that in a second step the same measurements can be carried out again with a single crystal turned through 90° about the longitudinal centre axis M.

Figure 6:
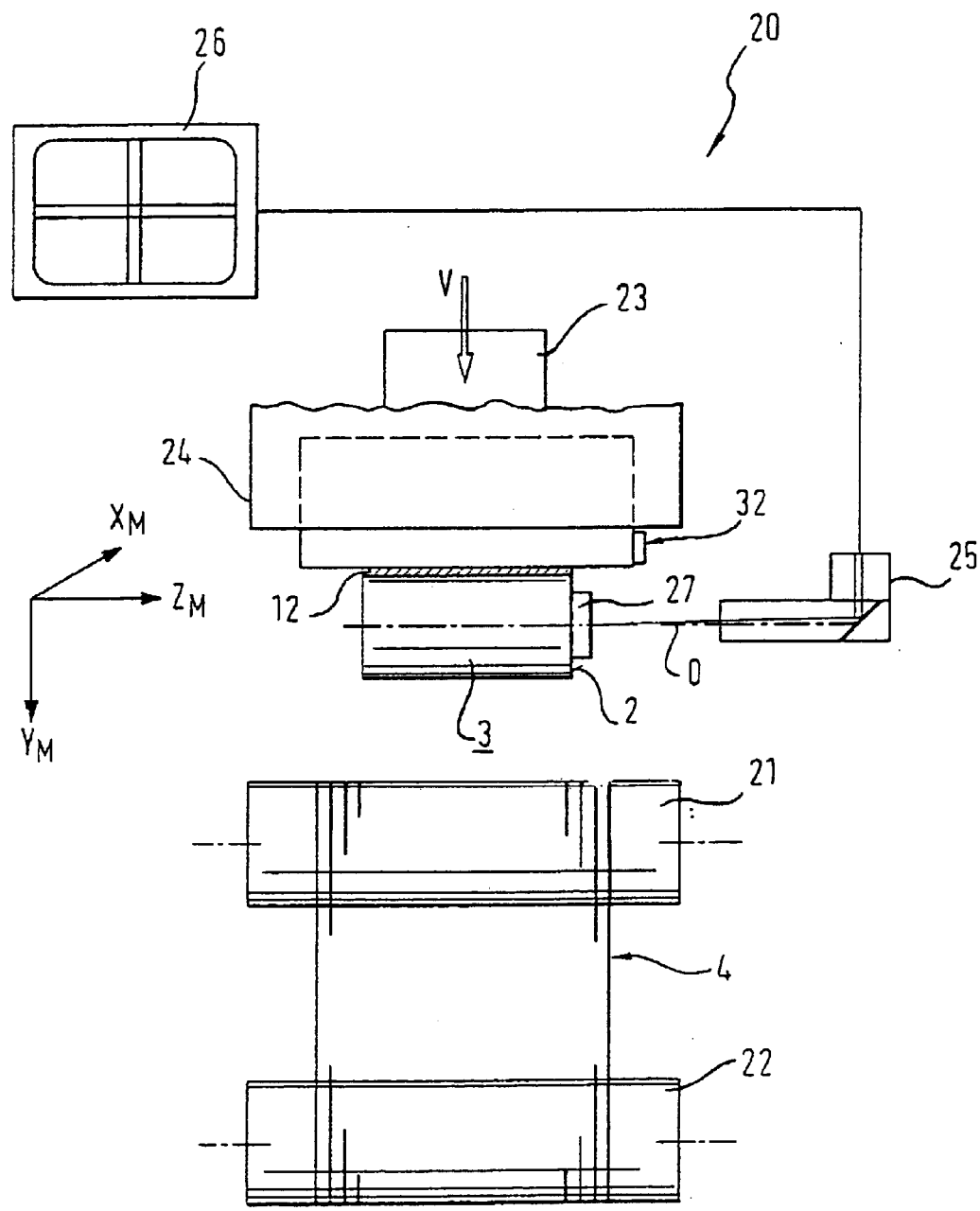
FIG. 6 a schematic view of an orienting device according to the invention in a wire sawing apparatus.
Figure 7:
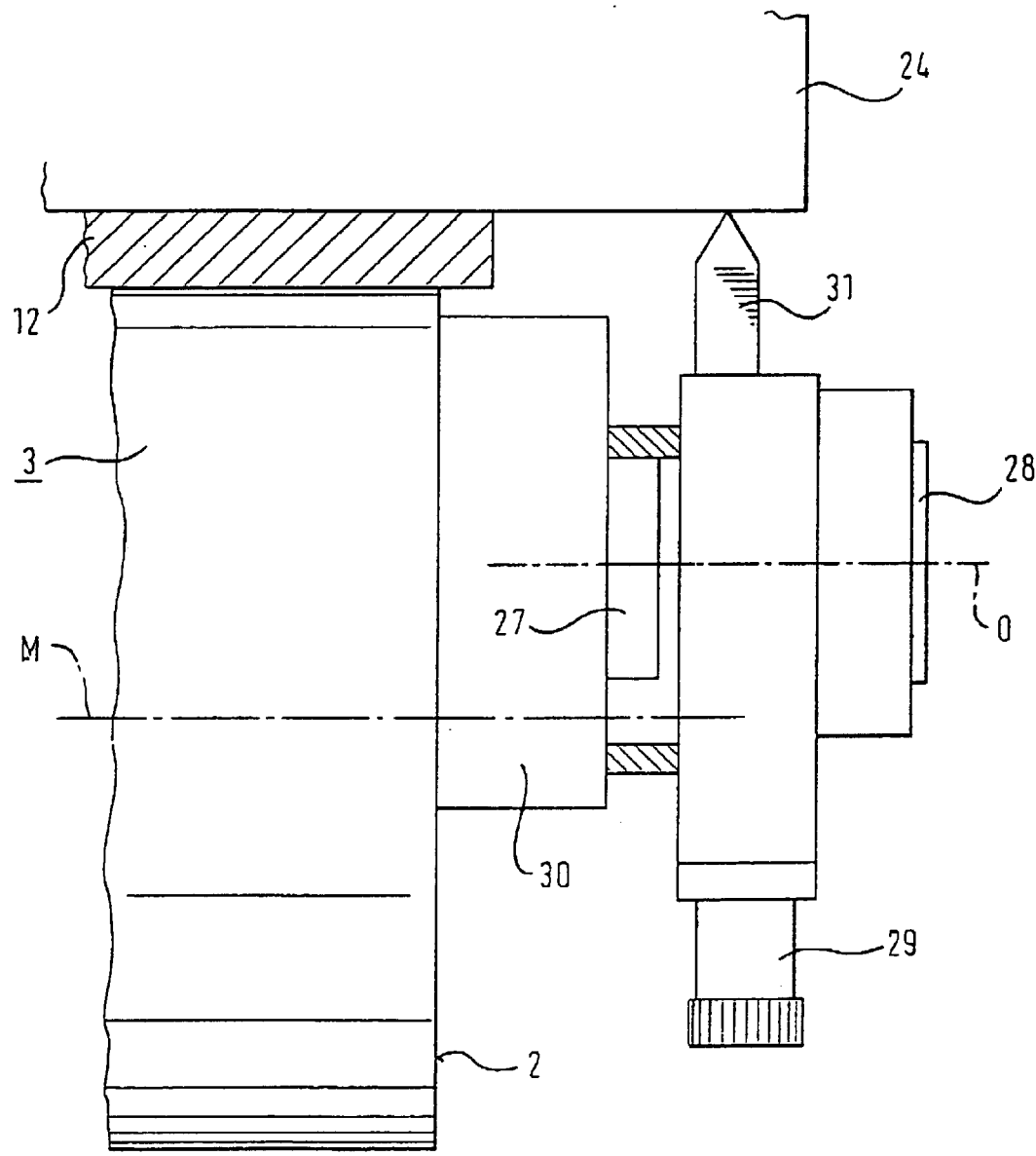
FIG. 7 a schematic view of a detail of FIG. 6.

As can be seen from FIGS. 6 and 7, an apparatus for cutting the single crystal which in this embodiment is constructed as a wire sawing apparatus 20 comprises wire rollers 21 over which the wire area 4 is guided in a horizontal direction, and guide rollers 22 located thereunder for return of the wire area below the actual wire plane in which cutting takes place. Above the wire area 4 is provided a feed unit 23 with which the single crystal is movable via the sawing substrate 12, which is attached to an X-Y positioning unit 24, in a vertical direction relative to the wire area at a given feed rate v. The X-Y positioning unit 24 is constructed so as to be able to displace the single crystal 3 referred to a coordinate system on the machine side $X_M$, $Y_M$, $Z_M$ in a direction parallel to the wire area 4, which is the $X_M$ direction, and in a direction perpendicular to the wire area 4, which is the $Y_M$ direction. The pivot range is about ±5° in the $X_M$ direction and about ±2° in the $Y_M$ direction. There is further provided an autocollimation telescope 25 which is identical with the autocollimation telescope 14 of the apparatus 10, whose optical axis O lies in a plane parallel to the wire area 4. The autocollimation telescope 25 is further arranged in such a way that its optical axis when the single crystal is installed lies approximately at the level of the centre axis of the single crystal. An evaluating unit 26 is provided for evaluating the angle measurement of the autocollimation telescope.

Further, the apparatus 20 includes a mirror 27 which is identical with the mirror 17 of the apparatus 10 and which is fixed by means of a vacuum mechanism, not shown, to the end face 2 of the single crystal 3 facing towards the autocollimation telescope 25. Further, an optical wedge plate 28 is provided in a rotatable socket 29 for producing a given beam deflection of e.g. 2°. Mirror 27 and wedge plate 28 are attached to a holder 30 which contains the vacuum mechanism. Also provided is a stop 31 which fixes a predefined distance between the mirror 27 with the wedge plate 28 and the X-Y positioning device 24.

To adjust the whole apparatus, there is further provided a reference face 32 which is attached to the feed unit 23 opposite the autocollimation telescope 25. The reference face has high planarity and mechanical stability and an easy-to-clean surface for easily removing dirt prior to measurement. By means of a camera, not shown, which can be mounted directly on the reference face, the reference face can be oriented in the horizontal plane parallel to the wire area 4.

Operation of the apparatuses 10 and 20 according to the invention is as follows. First the single crystal 3 is, as shown in FIG. 5b, stuck with the flat 7 onto the sawing substrate 12, with the aid of a stop, not shown, in a given angular orientation to the sawing substrate 12. The angle here is selected so that the flat 7 is oriented in the azimuthal direction in such a way that the given crystallographic direction K is at a predetermined angle ρ to the feed direction V at which the constraining forces acting on the wire almost cancel each other out, in order thus to be able to set the maximum possible feed rate. Then, as shown in FIG. 5a, the single crystal 3 together with the sawing substrate 12 is inserted on the holder 11 of the apparatus for determining the orientation of the crystallographic plane relative to the end face 2 of the single crystal by means of a vacuum mechanism, not shown. The vacuum mechanism allows the single crystal 3 to rest directly on the surface 11a of the holder 11. Then the holder 11 is moved into a given height position, so that the end face 2 of the single crystal is located in the focal plane of the X-ray goniometer. Then the mirror 17 is placed and fixed on the end face 2 by means of the vacuum mechanism. Next an angle measurement of the mirror surface is made by means of the autocollimation telescope 14, by determining a deviation of reflected cross hairs from the cross hairs projected onto the mirror surface. As the surface of the mirror 17 is oriented parallel to the end face 2 of the single crystal 3 and the optical axis O of the autocollimation telescope 14 is perpendicular to the surface 11a of the holder 11 which forms the reference face, with this measurement the angular adjustment of the mirror surface or of the end face of the single crystal relative to the surface 11a of the holder 11 can be determined.

Alternatively, the single crystal is measured without the sawing substrate, the orientation of the flat in the X-ray device being defined by a stop, for example.

The desired crystallographic plane, for example the (100) plane, is in general not parallel to the end face 2 of the single crystal 3. To determine the direction of the crystallographic plane, the Bragg reflection is measured with the X-ray goniometer 15, 16 which for this purpose is moved within a predefined angular range. The X-ray tube 15 and the detector 16 are for this purpose located in the known manner at a fixed angular distance from each other and are moved in an arc within the given angular range. The Bragg reflection indicates the angle which the crystallographic plane forms with the surface 11a of the holder 11. The X-ray goniometer measurement is repeated, the single crystal being rotated through 90°. Two vectors are obtained by the optical and X-ray goniometer measurements, the X-ray measurements ($x_{100}$, $y_{100}$) and the optical measurements ($X_{OF}$, $Y_{OF}$) with respect to the zero point of the orientation system. The difference between the two vectors yields the orientation of the crystallographic (100) plane to the crystal end face 2 independently of all external reference systems such as kit bars, thrust pieces, fastening chucks, etc. After this measurement, the orientation of the crystallographic (100) plane with respect to the end face 2 of the single crystal is known. This yields correction values for the X-Y positioning in the wire saw for adjusting a desired misorientation.

Next, the position of the end face 2 on the crystal is measured on the wire saw 20 by means of the identical autocollimation telescope 25 and the identical plane-parallel mirror 27. The zero-point adjustment of the X-Y positioning unit 24 in the coordinate system on the machine side $X_M$, $Y_M$ is made in this case by means of the reference face 23. In the $Y_M$ direction, that is, in the feed direction, the adjustment is made only once at the factory, for example with a dial gauge. The zero-point definition in the $X_M$ direction, i.e. in the wire plane, takes place at each change of roller of the cutting wire. For this purpose the reference face 32 is oriented horizontally on the wire area with a camera which is attached to the reference face and which determines the X position relative to a reference wire of the wire area.

To adjust the autocollimation telescope 25, the feed unit 23 is moved into the reference position, i.e. the reference face 32 is located in the optical axis of the autocollimation telescope 25, and the mirror 27 is placed on the reference face and also the position of the autocollimation telescope is measured. Then electronic referencing is effected with the aid of the reference face 32, the mirror 27 being drawn onto the reference face 32 by means of the vacuum fastening device. Then the mirror 27 is removed and the feed unit is moved into the loading or orienting position and the single crystal 3 is attached to the sawing substrate 12. Then the mirror 27 is attached to the crystal end face 2 and the angular adjustment of the end face 2 is measured with the autocollimation telescope 25. Then the correction values obtained from the measurement in the apparatus 10 are entered and the horizontal and vertical position adjustments of the single crystal are made, so that the crystallographic plane exhibits the predefined angle to the wire area. The mirror is removed and cutting is carried out.

With the method described, the azimuthal angular adjustment of the given crystallographic direction K is maintained, and operation can be carried out at high feed rates compared with the state of the art. The feed rates are, for example for cutting a 6-inch GaAs single crystal, approximately fourfold compared with the traditional orientation, at which it is not possible to suitably adjust the azimuthal angular position.

In a modification, the desired misorientation is taken into consideration by providing the wedge plate. In a further modification of the cutting apparatus according to the invention, the single crystal is rotatable in the cutting apparatus about its axis $N_0$ shown in FIG. 1, which is perpendicular to the wafer surface, in order to adjust the optimum angle to minimise the cutting forces. Alternatively, it is also possible to adjust the optimum angle to minimise the cutting forces by tilting the wire area. Preferably, a measuring device is then provided to measure the deflection of the cutting apparatus during cutting.

Instead of the deflection in the measuring apparatus 10, a contactless distance measuring system can also be used for detection of the orientation of the flat.

All errors due to adhesion or contamination of stops, reference faces, etc. are eliminated, as measurements can be made directly on the wire sawing apparatus 20. The apparatus described and the method allow high-precision direct measurement on the wire saw without a safety risk. Further, the angle measurement with the autocollimation method is independent of the measuring distance, so that it is possible to mount the autocollimation telescope 25 outside the cutting space. For cutting, the corresponding protective hood can then be closed. The X-Y positioning unit allows vertical and horizontal adjustment of the components of the misorientation, so that the processing direction of the crystal is freely selectable at any time and can be used as a control variable for the wire deflection.

The invention is not confined to a wire sawing apparatus, but can also be used in an inner hole cutting apparatus, for example.

What is claimed is:

1. An apparatus for cutting single crystals having a longitudinal center axis (M), the apparatus comprising:
    a cutting device for cutting off wafers from the single crystal, the cutting device comprising a wire saw having a plurality of parallel wires which form a wire cutting plane;
    a feed device for moving the crystal in a feed direction (V) essentially perpendicular to its longitudinal center axis relative to the cutting device;
    a holder for the single crystal, wherein the single crystal can be positioned in the cutting apparatus such that a predetermined crystallographic direction (K) has a predetermined angle relative to the feed direction (V);
    an angle measuring device for measuring the orientation of an end face of the single crystal relative to the wire plane and;
    an orienting device provided in the apparatus for orienting the single crystal relative to the cutting device, the orienting device being structued and arranged to rotate the single crystal about an axis defined by the feed direction and an axis which is perpendicular to the plane which is defined by the longitudinal center axis (M) and the feed direction (V);
    wherein the orienting device comprises an X-Y positioning unit with which the single crystal is displaceable in a plane parallel to the wire plane and in a plane perpendicular to the wire plane.

2. The apparatus according to claim 1, wherein the angle measuring device comprises a mirror that can be fixed to the end face of the single crystal and an autocollimation telescope having an optical axis (O) that is perpendicular to a cutting plane.

3. The apparatus according to claim 2, further comprising a vacuum device for attaching the mirror to the end face of the single crystal.

4. The apparatus according to claim 1, wherein the holder for the single crystal is structured and arranged to be positioned in the cutting apparatus such that a predetermined external feature of the single crystal is oriented in a predetermined position rotated about the longitudinal center axis (M).

5. A method for cutting a single crystal in a cutting machine in which wafers are cut off from the single crystal by movement of the single crystal in a feed direction (V) relative to a cutting device, the method comprising the steps of:
    determining an angle between a selected crystallographic plane and an external surface of the single crystal outside of the cutting machine;
    measuring the orientation of the external surface of the single crystal in the cutting machine;
    positioning the single crystal in the cutting machine on the basis of the orientation of the external surface such that the selected crystallographic plane forms a predetermined angle with the feed direction; and
    cutting the single crystal into wafers;
    wherein determining the angle between the crystallographic plane and the external surface comprises:
        measuring a first angle formed by the crystal surface with a reference axis using an autocollimation method;
        measuring a second angle of the crystallographic plane relative to the reference axis by X-ray goniometry; and
        determining the difference between the first and second measured angles.

6. The method according to claim 5, further comprising adjusting the angular position of a given crystallographic direction (K) of the single crystal in the cutting plane such that, during cutting of the single crystal, the forces acting on the cutting device are minimized.

7. An apparatus for cutting single crystals having a longitudinal center axis (M), the apparatus comprising:
    a cutting device for cutting off wafers from the single crystal;
    a feed device for moving the crystal in a feed direction (V) essentially perpendicular to its longitudinal center axis relative to the cutting device;
    a holder for the single crystal, wherein the single crystal can be positioned in the cutting apparatus such that a predetermined crystallographic direction (K) has a predetermined angle relative to the feed direction (V);
    an orienting device provided in the apparatus for orienting the single crystal relative to the cutting device, the orienting device being structued and arranged to rotate the single crystal about an axis defined by the feed direction and an axis which is perpendicular to the plane which is defined by the longitudinal center axis (M) and the feed direction (V);
    further comprising a analytical device for determining the orientation of a crystallographic plane relative to a crystal surface, wherein the analytical device comprises:
        a second holder having a reference axis for holding the single crystal such that a surface to be measured is exposed;

an angle measuring device for measuring an angle of the surface to be measured forms with the reference axis of the second holder; and an X-ray measuring device for determining the angle of the crystallographic plane relative to the reference axis.

8. The apparatus according to claim 7, wherein the single crystal comprises a cylinder and the surface to be measured is an end face of the cylinder, and the second holder comprises a plane surface to which the single crystal can be fixed with an end face opposite the surface to be measured, and wherein the reference axis is normal to the plane surface.

9. The apparatus according to claim 7, wherein the angle measuring device comprises a mirror that can be arranged on the surface to be measured and an autocollimation telescope whose optical axis (O) coincides with the reference axis.

10. The apparatus according to claim 7, wherein the X-ray measuring device comprises an X-ray goniometer, which includes an X-ray tube and a detector that are movable together within an angular range about the reference axis for measuring Bragg reflections for the crystallographic plane.

11. The apparatus according to any of claims 7, wherein the second holder is movable in a direction of the reference axis.

12. The apparatus according to claim 7, wherein the second holder comprises a vacuum suction device for fixing the single crystal by means of partial pressure or vacuum.

13. The apparatus according to claim 7, wherein the second holder comprises a stop with which the single crystal can be fixed in a plane in a perpendicular to the reference axis predetermined angular orientation.

14. An apparatus for determining the orientation of a crystallographic plane of a single crystal relative to a crystal surface, said apparatus comprising:

a holder having a reference axis for holding the single crystal such that the crystal surface to be measured is exposed;

an angle measuring device for measuring the angle of the crystal surface to be measured relative to the reference axis of the holder; and an X-ray measuring device for determining the angle of the crystallographic plane relative to the reference axis;

wherein the angle measuring device includes a mirror arranged on the surface to be measured and an autocollimation telescope having an optical axis which coincides with the reference axis.

15. The apparatus according to claim 14, wherein the single crystal comprises a cylinder and the crystal surface to be measured is an end face of the cylinder, wherein the holder comprises a plane surface to which the single crystal can be fixed with a second end face opposite the crystal surface to be measured, and wherein the reference axis is normal to the plane surface.

16. The apparatus according to claim 14, wherein the X-ray measuring device comprises a X-ray goniometer which includes an X-ray tube and a detector that are movable together within an angular range about the reference axis for measuring Bragg reflections for the crystallographic plane.

17. The apparatus according to claim 14, wherein the holder is movable in a direction of the reference axis.

18. The apparatus according to claim 14, wherein the holder comprises a vacuum suction device for fixing the single crystal by means of partial pressure or vacuum.

19. The apparatus according to claim 14, wherein the holder comprises a stop with which the single crystal can be fixed in a predetermined angular orientation in a plane perpendicular to the reference axis.

20. A method for determining the orientation of a crystallographic plane of a single crystal relative to a crystal surface which can be used in an application for the cutting of the single crystal, the method comprising the steps of:

measuring a first angle that the crystal surface forms with a reference axis by an autocollimation method;

measuring a second angle of the crystallographic plane relative to the reference axis by X-ray goniometry; and determining the difference between the first and second measured angles.

21. An apparatus for cutting single crystals having a longitudinal center axis (M), the apparatus comprising:

a cutting device for cutting off wafers from the single crystal, the cutting device comprising a wire saw having a plurality of parallel wires which form a wire cutting plane;

a feed device for moving the crystal in a feed direction (V) essentially perpendicular to its longitudinal center axis relative to the cutting device;

a holder for the single crystal, wherein the single crystal can be positioned in the cutting apparatus such that a predetermined crystallographic direction (K) has a predetermined angle relative to the feed direction (V);

an orienting device provided in the apparatus for orienting the single crystal relative to the cutting device, the orienting device being structured and arranged to rotate the single crystal about an axis defined by the feed direction and an axis which is perpendicular to the plane which is defined by the longitudinal center axis (M) and the feed direction (V), wherein the orienting device comprises a X-Y positioning unit with which the single crystal is displaceable in a plane parallel to the wire plane and in a plane perpendicular to the wire plane; and a reference device for the X-Y positioning unit.

22. An apparatus for cutting single crystals having a longitudinal center axis (M), the apparatus comprising:

a cutting device for cutting off wafers from the single crystal, the cutting device comprising a wire saw having a plurality of parallel wires which form a wire cutting plane;

a feed device for moving the crystal in a feed direction (V) essentially perpendicular to its longitudinal center axis relative to the cutting device;

a holder for the single crystal, wherein the single crystal can be positioned in the cutting apparatus such that a predetermined crystallographic direction (K) has a predetermined angle relative to the feed direction (V);

an orienting device provided in the apparatus for orienting the single crystal relative to the cutting device, the orienting device being structured and arranged to rotate the single crystal about an axis defined by the feed direction and an axis which is perpendicular to the plane which is defined by the longitudinal center axis (M) and the feed direction (V), wherein the orienting device comprises a X-Y positioning unit with which the single crystal is displaceable in a plane parallel to the wire plane and in a plane perpendicular to the wire plane; and a wedge plate having a given wedge angle for adjusting a predetermined angle offset of the X-Y orientation of the single crystal.

23. The apparatus according to claim 22, wherein the wedge plate is rotatable in the cutting plane about the longitudinal center axis of the single crystal such that a given azimuthal orientation of the wedge angle is adjustable.

* * * * *